United States Patent [19]

Evans

[11] 4,251,537

[45] Feb. 17, 1981

[54] HYPOTENSIVE 3,4-DIHYDRO-2,2-DIMETHYL-4-AMINO-2H-BENZO[B]PYRAN-3-OLS

[75] Inventor: John M. Evans, Roydon, England

[73] Assignee: Beecham Group Limited, England

[21] Appl. No.: 970,199

[22] Filed: Dec. 18, 1978

Related U.S. Application Data

[63] Continuation of Ser. No. 776,976, Mar. 14, 1977, abandoned.

[30] Foreign Application Priority Data

Apr. 2, 1976 [GB] United Kingdom ............... 13536/76
Aug. 10, 1976 [GB] United Kingdom ............... 33178/76

[51] Int. Cl.$^3$ .................. A61K 31/445; C07D 405/04
[52] U.S. Cl. ............................... 424/267; 260/326.34; 260/326.5 SF; 260/326.5 S; 260/326.5 CA; 260/345.2; 424/274; 424/283; 544/58.7; 544/62; 544/151; 544/376; 546/196

[58] Field of Search ....... 260/345.2, 326.34, 326.5 SF, 260/326.5 S, 326.5 CA; 546/196; 424/267, 274, 283

[56] References Cited

U.S. PATENT DOCUMENTS 4,048,317   9/1977   Watts ............................... 546/196 X

OTHER PUBLICATIONS

Martin, E., (Ed.), HUSA's Pharmaceutical Dispensing, 5th ed., Mack Pub. Co., Easton, Pa., 1959, pp. 583-584.

Primary Examiner—Alan L. Rotman
Assistant Examiner—Richard A. Schwartz
Attorney, Agent, or Firm—Jacobs & Jacobs

[57] ABSTRACT

Amino chromanols, their preparation and anti-hypertensive compositions containing the compounds in hypotensive amounts with a pharmaceutically acceptable carrier for oral or parenteral administration. Pharmaceutically acceptable salts and O-acyl, particularly O-acetyl, derivatives are described. The compounds exist as racemates and optically active isomers.

31 Claims, No Drawings

HYPOTENSIVE 3,4-DIHYDRO-2,2-DIMETHYL-4-AMINO-2H-BENZO[B]PYRAN-3-OLS

CROSS-REFERENCE

This is a continuation of Ser. No. 776,976 filed Mar. 14, 1977, now abandoned.

The present invention relates to novel amino chromanols, to their preparation and to anti-hypertensively effective compositions containing them.

Belgian Pat. No. 829611 discloses a group of hypotensive agents of the formula (O):

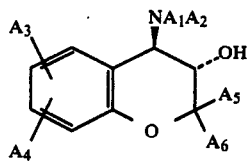

and acid addition salts thereof wherein $A_1$ is a hydrogen atom or a $C_{1-9}$ hydrocarbon group optionally substituted by a hydroxyl or $C_{1-6}$ alkoxyl group; $A_2$ is a hydrogen atom or $C_{1-6}$ alkyl group or $NA_1A_2$ is a 3–8 membered heterocyclic group optionally substituted by one or two methyl groups; $A_3$ is a hydrogen or halogen atom or a $C_{1-6}$ alkyl, $C_{2-6}$ alkenyl, $C_{1-6}$ alkoxyl, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrile or $XOA_7$, $XSA_7$, $XSO_2A_7$, $XNHA_7$, $XNA_7COA_8$, $XNA_7SO_2A_8$ or $XNA_7CO_2A_8$ group wherein X is an alkylene group of 1–4 carbon atoms, $A_7$ is an alkyl group of 1–4 carbon atoms and $A_8$ is an alkyl group of 1–4 carbon atoms; and $A_4$ is a hydrogen or halogen atom or $A_3$ together with $A_4$ forms a —CH=CH—CH=CH—, —NH—CH=CH—, —CH$_2$—CH$_2$—CH$_2$— or —CH$_2$—CH$_2$—CH$_2$—CO— system; $A_5$ is a hydrogen atom or a $C_{1-6}$ alkyl or phenyl group; and $A_6$ is a hydrogen atom or a $C_{1-6}$ alkyl or phenyl group.

It has now been discovered that a distinct group of amino chromanols have useful anti-hypertensive activity.

Accordingly the present invention provides compounds of the formula (I):

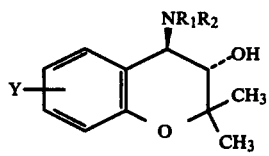

wherein $R_1$ is a hydrogen atom or an alkyl group of up to 4 carbon atoms optionally substituted by a chlorine or bromine atom or by a hydroxyl group or by an alkoxyl group of up to 4 carbon atoms or by an acyloxy group of up to 4 carbon atoms and $R_2$ is a hydrogen atom or an alkyl group of up to 4 carbon atoms or $R_1$ is joined to $R_2$ so that together with the nitrogen atom to which they are attached they form a 5-, 6- or 7-membered heteroalicyclic ring which is optionally substituted by methyl; Y is a group $CO.R_3$, $CO_2R_3$, $SO.R_3$, $SO_2.R_3$, $SO.OR_3$, $SO_2.OR_3$, $CH(OH)R_3$, $C(R_3)$=NOH, $C(R_3)$=NNH$_2$, $CONH_2$, $CO.NR_4R_5$, $SO.NR_4R_5$ or $SO_2NR_4R_5$ where $R_3$ and $R_4$ are each independently a hydrocarbon group of up to 8 carbon atoms or such a group inertly substituted by a chlorine or bromine atom or by a hydroxyl group or by an alkoxyl group of 1–4 carbon atoms or by an acyloxy group of up to 4 carbon atoms or by 3 fluorine atoms attached to the same carbon atom and $R_5$ is a hydrogen atom or an alkyl group of up to 4 carbon atoms; and salts thereof and O-acyl derivatives thereof wherein the O-acyl moiety contains up to 18 carbon atoms.

Suitably Y is a $CO.R_3$, $CO_2R_3$, $SO.R_3$, $SO_2R_3$, $SO.OR_3$, $SO_2.OR_3$, $CO.NR_4R_5$, $SO.NR_4R_5$ or $SO_2NR_4R_5$ group.

Suitably Y is a $CH(OH)R_3$, $C(R_3)$=NOH or $C(R_3)$=NNH$_2$ group.

Suitable groups $R_1$ include the hydrogen atom and the methyl, ethyl, isopropyl, t-butyl, β-hydroxyethyl, β-acetoxyethyl, β-methoxyethyl, γ-chloropropyl and the like.

Suitable groups $R_2$ include the methyl, ethyl, isopropyl and t-butyl groups and hydrogen.

Suitable cyclic groups $NR_1R_2$ include groups of the sub-formula (a):

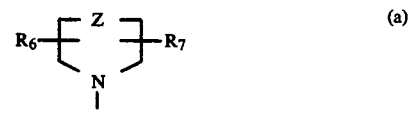

wherein Z is a bond joining the two carbon atoms or is a $CH_2$, $CH_2.CH_2$, $CH_2.CH_2.CH_2$, CH:CH, O, S or NCH$_3$ group; $R_6$ is a hydrogen atom or a methyl group and $R_7$ is a hydrogen atom or a methyl group.

Particularly suitable groups $NR_1R_2$ include NHCH$_3$, NH(CH$_2$)$_3$Cl, N(CH$_3$)$_2$, NH.CH(CH$_3$)$_2$, NH.C(CH$_3$)$_3$ and those of the sub-formula (b):

wherein $Z^1$ is a bond joining the two carbon atoms or is a —CH$_2$—, —CH$_2$.CH$_2$—, —CH$_2$.CH$_2$.CH$_2$— or —CH:CH— group or an oxygen atom.

The preferred groups $NR_1R_2$ are the piperidino and pyrralidine groups.

Preferred compounds of the formula (I) include those of the formulae (II) and (III):

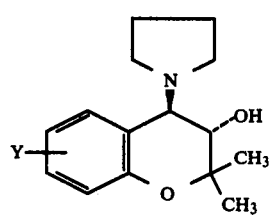

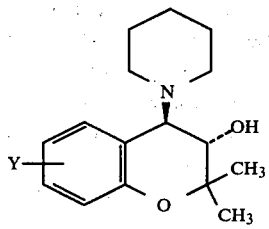

and salts and O-acyl derivatives thereof wherein Y is as defined in relation to formula (I).

Suitably Y is a $CO.R_3$, $CO_2R_3$, $SO.R_3$, $SO_2.R_3$, $SO.OR_3$, $SO_2.OR_3$, $CO.NR_4R_5$, $SO.NR_4R_5$ or $SO_2NR_4R_5$ group where $R_3$, $R_4$ and $R_5$ are as defined in relation to formula (I).

Suitably Y is a $CH(OH)R_3$, $C(R_3)=NOH$ or $C(R_3)=NNH_2$ group where $R_3$ is as defined in relation to formula (I).

Particularly suitable values for Y in the compounds of formulae (I)–(III) are the $CO.R_3$, $CO_2R_3$ or $CO.NR_4R_5$ groups, especially the $CO_2R_3$ group.

Further particularly suitable values for Y in the compounds of the formulae (I)–(III) are the $SO_2.R_3$, $SO_2.OR_3$ and $SO_2NR_4R_5$ groups.

Another particularly suitable value for Y in the compounds of the formulae (I)–(III) is the $CH(OH)R_3$ group.

Preferred values for $R_3$ in relation to a compound of the formulae (I)–(III) are the methyl and ethyl groups.

A preferred O-acyl derivative of the compounds of the formulae (I)–(III) is the O-acetyl derivative.

Most suitably the O-acyl derivatives of the compounds of the formulae (I)–(III) are those wherein the acyl moiety is of the formula —$CO.R^1$ where $R^1$ is an n-alkyl group of 1–6 carbon atoms optionally substituted by a phenyl group.

Most suitably in the compounds of the formulae (I)–(III) the group Y is attached to the 6- or 7- position of the chroman nucleus.

One preferred position of attachment of the group Y in the compounds of the formulae (I)–(III) is the 6-position of the chroman nucleus.

Favoured values for Y include the 6—$CH(OH)R_3$, 6—$CO_2R_3$, 6—$C(R_3)=NOH$, $CO.R_3$, 6—$CO.NH_2$ and 6—$C(R_3)=NNH_2$ groups more suitably where $R_3$ is a methyl or ethyl group and especially where $R_3$ is a methyl group.

Acid addition salts of the amino compounds of formulae (I)–(III) may be made with acids in conventional manner. Suitable salt-forming acids include hydrochloric, hydrobromic, sulphuric, phosphoric, methanesulphonic, p-toluenesulphonic, acetic, propionic, succinic, citric, tartaric, mandelic, lactic, gluconic and other pharmaceutically acceptable organic or inorganic acids.

The compounds of the invention exist in optically active forms. Those skilled in the chemical arts will realise that racemic mixtures of amino compounds can often be separated into pure optical isomers using such techniques as fractional crystallisation using optically active acids and the like.

Particularly suitable compounds of this invention include 6-acetyl-3,4-dihydro-2,2-dimethyl-trans-4-piperidino-2H-benzo[b]pyran-3-ol, 6-acetyl-3,4-dihydro-2,2-dimethyl-trans-4-pyrrolidino-2H-benzo[b]pyran-3-ol, 6-carbomethoxy-3,4-dihydro-2,2-dimethyl-trans-4-piperidino-2H-benzo[b]pyran-3-ol, 6-carbomethoxy-3,4-dihydro-2,2-dimethyl-trans-4-pyrrolidino-2H-benzo[b]pyran-3-ol, 1-[trans-2,2-dimethyl-3-hydroxy-4-piperidinochroman-6-yl]-ethanone oxime, 1-[trans-2,2-dimethyl-3-hydroxy-4-pyrrolidinochroman-6-yl]-ethanone oxime, 6-carboxamido-3,4-dihydro-2,2-dimethyl-trans-4-piperidino-2H-benzo[b]-pyran-3-ol, and 6-carboxamido-3,4-dihydro-2,2-dimethyl-trans-4-pyrrolidino-2H-benzo[b]pyran-3-ol and their pharmaceutically acceptable salts and O-acyl derivatives such as their O-acetyl derivatives.

A further aspect of this invention provides pharmaceutical compositions suitable for the treatment of hypertension comprising a compound of the invention and a pharmaceutically acceptable carrier. Such compositions may be suitable for parenteral or oral administration, but in general, oral compositions are preferred because of convenience of administration. Frequently, it is advantageous to administer compounds of the invention together with an adrenergic $\beta$-blocking agent.

The compositions of this invention are preferably in the form of unit dosage forms such as tablets or capsules. Such unit dosage forms will usually contain from 0.5 to 100 mg, for example, 2 to 50 mg, and will usually be administered from 1 to 6 times a day so that the daily dose for a 70 kg human is from 2 to 150 mg, for example, 10 to 100 mg.

The compositions of this invention may be formulated in conventional manner, for example, in a manner similar to that used for known anti-hypertensive agents such as α-methyldopa, propranalol, guanethidine and the like. In conventional manner, the compositions of this invention may contain further active agents such as additional anti-hypertensive agents, diuretics and the like.

The compounds of formula (I) may be prepared by the reaction of an amine of the formula $NHR_1R_2$ with an epoxide of the formula (IV):

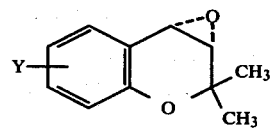

wherein Y is as defined in relation to formula (I).

The reaction of the amine and epoxide may be carried out at any non-extreme low, medium or high temperature (for example, −10° C. to 200° C.) but in general ambient or slightly elevated temperatures are most suitable (for example, 12° C. to 100° C.). The reaction is normally carried out in the presence of a solvent such as alkanolic or ketonic solvent (for example, methanol, ethanol, propanol, acetone or methylethylketone).

It has been found that the reaction frequently proceeds smoothly and sufficiently if the reaction is carried out in warmed or refluxing ethanol.

The above reaction has been found to give a trans product substantially free from the cis-isomer.

The oximes and hydrazines of formula (I) may also be prepared from the corresponding ketone by reaction with hydroxylamine or hydrazine in conventional manner, for example in an alkanolic solvent such as methanol or ethanol at a non-extreme temperature, for example any convenient temperature from 0° C. to 100° C. such as the reflux temperature of the solution.

Those compounds of the formula (I) wherein Y is a CH(OH)$R_3$ group may also be prepared by the reduction of the corresponding compound of the formula (I) wherein Y is a CO.$R_3$ group under conventional conditions, for example in an alkanolic solvent such as aqueous methanol or ethanol at a non-extreme temperature, for example 0° C. to 50° C., using a conventional reducing agent such as sodium borohydride, lithium aluminium hydride, hydrogen in the presence of a transition metal catalyst or the like reaction.

The useful intermediates of the formula (IV) may be prepared by processes analogous to those described in Belgian Pat. No. 829611.

A suitable method of preparing the compounds is as follows:

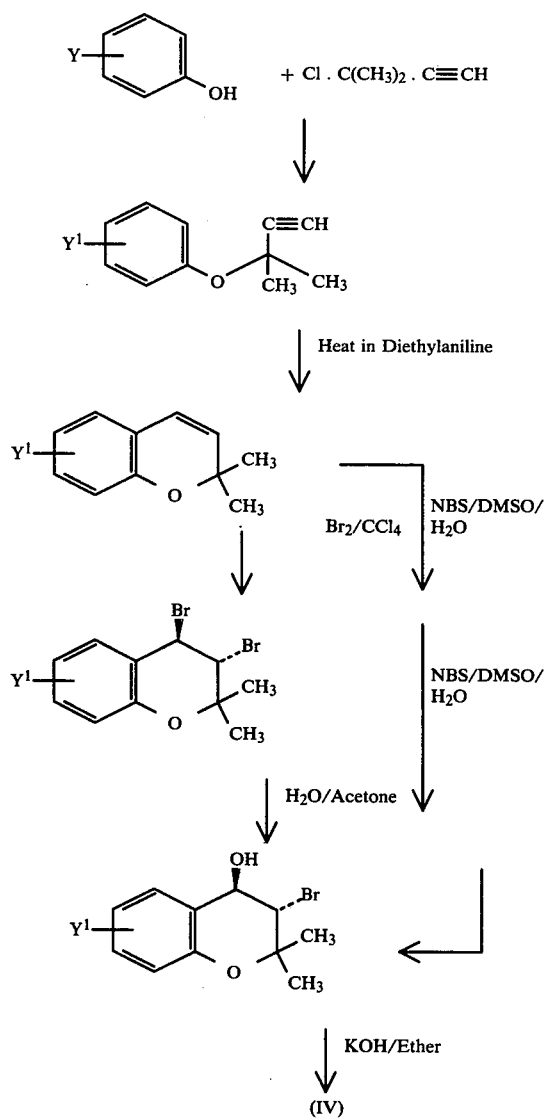

In the preceding scheme $Y^1$ is an inert group within Y. Chemically reactive groups within Y such as oxime, hydrazine or alkanolic groups, may be prepared from corresponding ketones as previously outlined.

The reaction conditions for the conversions shown in the scheme are conventional and will be understood by the skilled man from the available literature such as Belgian Pat. No. 829611.

Other groups Y may be prepared from analogous moieties in known manner, for example a nitrile may be hydrolysed to yield a carboxamido group.

The O-acyl derivatives of the compounds of formula (I) may be prepared by conventional methods of acylation such as by reaction with an acid anhydride, acid halide or the like.

The following Examples illustrate the invention:

EXAMPLE 1

(a) 6-Acetyl-3,4-dihydro-2,2-dimethyl-trans-4-piperidino-2H-benzo[b]pyran-3-ol and (b) 6-Acetyl-3,4-dihydro-2,2-dimethyl-trans-4-isopropylamino-2H-benzo[b]pyran-3-ol hydrochlorides p-Hydroxyacetophenone (33.66 g), sodium hydroxide pellets (14.80 g), 40% benzyltrimethylammonium hydroxide in methanol (51.75 g) and 3-methyl-3-chlorobutyne (61.25 g) were stirred in water (225 ml) and dichloromethane (225 ml) for 4 days at room temperature. After separation of the layers, the aqueous layer was extracted twice with chloroform, and the combined organic phase evaporated leaving a viscous liquid which was taken up in ether and washed three times with 10% sodium hydroxide solution and once with water before drying over sodium sulphate. Removal of drying agent and solvent, and distillation at 1.0 mm Hg gave an oil (55.31 g) which was dissolved in N,N-diethylaniline (275 ml) and heated at 210°–220° C. for 8 hours under nitrogen. The major part of the solvent was distilled off, and treatment of an ethereal solution of the residue with anhydrous ethereal hydrogen chloride precipitated the remainder, leaving an oil after solvent evaporation which was distilled giving 6-acetyl-2,2-dimethyl-2H-benzo[b]pyran (40.02 g), b.p. 100°–102°/0.2 mm Hg.

Addition to this chromene (39.07 g) dissolved in dimethyl sulphoxide (390 ml) containing water (7.00 ml), of N-bromosuccinimide (69.00 g) with vigorous stirring and cooling, followed by dilution with water and extraction via ethyl acetate gave 6-acetyl-trans-3-bromo-3,4-dihydro-2,2-dimethyl-2H-benzo[b]pyran-4-ol as pale pink crystals (44.65 g) of m.p. 109°–113° C. from ethyl acetate. The bromohydrin (39.35 g) was vigorously stirred in dry ether (3.9 liters) containing potassium hydroxide pellets (39.00 g) for 4 days at room temperature. Filtration and evaporation followed by recrystallisation from 60°–80° petroleum ether yielded 6-acetyl-3,4-epoxy-3,4-dihydro-2,2-dimethyl-2H-benzo[b]pyran as cream coloured crystals (22.00 g) m.p. 75°–76° C.

This epoxide (10.00 g) and piperidine (3.5 ml) were refluxed in ethanol (100 ml) for 24 hours. Removal of solvent, addition of ether, washing with water before drying, followed by filtration and treatment of the ethereal solution with ethereal hydrogen chloride, gave a precipitate which was collected and washed with dry ether leaving 6-acetyl-3,4-dihydro-2,2-dimethyl-trans-4-piperidino-2H-benzo[b]pyran-3-ol hydrochloride as a white solid (12.33 g) m.p. 234°–236° C.

Similarly prepared from the epoxide was 6-acetyl-3,4-dihydro-2,2-dimethyl-trans-4-isopropylamino-2H-benzo[b]pyran-3-ol hydrochloride as a white solid of m.p. 250°–253° C.

EXAMPLE 2

1-[Trans-2,2-dimethyl-3-hydroxy-4-piperidinochroman-6-yl]-ethanone oxime methane sulphonate 6-Acetyl-3,4-dihydro-2,2-dimethyl-trans-4-piperidino-2H-benzo[b]pyran-3-ol (3.00 g), hydroxylamine hydrochloride (0.83 g) and sodium hydroxide pellets (0.50 g) were refluxed in methanol (150 ml) for 50 hours. After cooling the solvent was evaporated and the residue taken up in ether and washed with water until the washings were neutral, leaving a white solid (2.95 g) which was chromatographed on silica gel (100 g) using a gradient elution technique with ethyl acetate-60/80 petroleum ether. After elution of starting material, the antiepimer was obtained (1.37 g), pure by thin layer chromatographic and nmr analysis.

The oxime (0.77 g) dissolved in 'sodium dry' ether (20 ml) was treated with methane sulphonic acid (0.16 ml). A precipitate formed which was collected (0.93 g) and recrystallised from ethanol-ether giving 1-[trans-2,2-dimethyl-3-hydroxy-4-piperidino-chroman-6-yl]-ethanone oxime methane sulphonate as a white solid (0.70 g) m.p. 208.5°–210° C.

Similarly prepared was 1[trans-2,2-dimethyl-3-hydroxy-4-isopropylamino-chroman-6-yl]-ethanone oxime methane sulphonate of m.p. 215.5°–217° C.

EXAMPLE 3

1-Hydroxy-1-[trans-2,2-dimethyl-3-hydroxy-4-piperidinochroman-6-yl]ethane hydrochloride 6-Acetyl-3,4-dihydro-2,2-dimethyl-trans-4-piperidino-2H-benzo[b]pyran-3-ol (1.00 g) was dissolved in methanol (10 ml) and water (2 ml) and treated with sodium borohydride (0.10 g) with stirring at room temperature during 5 minutes. After an additional 2 hours stirring, the reaction mixture was diluted with water (100 ml). Extraction using diethyl ether gave 1-hydroxy-1-[trans-2,2-dimethyl-3-hydroxy-4-piperidinochroman-6-yl]-ethane (1.00 g) which was dissolved in dry ether and treated with ethereal hydrogen chloride giving the hydrochloride salt (0.90 g) m.p. 179°–181° C. as a white powder from ethanol-ether.

Similarly prepared was 1-hydroxy-1[trans-2,2-dimethyl-3-hydroxy-4-pyrrolidino-chroman-6-yl]ethane hydrochloride m.p. 203° C.

EXAMPLE 4

6-Carbomethoxy-3,4-dihydro-2,2-dimethyl-trans-4-pyrrolidino-2H-benzo[b]pyran-3-ol methane sulphonate To a stirred suspension of methyl p-hydroxybenzoate (50.0 g), anhydrous potassium carbonate (60.8 g) and potassium iodide (3.0 g) in acetone (500 ml) under nitrogen, was added 3-methyl-3-chlorobutyne (85.4 g) in acetone (100 ml). The suspension was stirred and heated to reflux temperature for a further 42 hours before cooling and filtering. Removal of solvent gave a gum which was taken up in diethyl ether and washed three times with 1 N sodium hydroxide solution, and once with water before drying over sodium sulphate. Removal of drying agent and solvent gave a gum (74.06 g) which was shown by nmr to be a mixture of the propargyl ether and dimethylchromene.

Cyclisation was completed by heating this mixture (74.00 g) in o-dichlorobenzene (150 ml) for 3.5 hours. Removal of solvent and distillation at 0.15 mm Hg gave the analytical sample (60.45 g) boiling at 114°–120° having a nmr spectrum in accord with that reported for 6-carbomethoxy-2,2-dimethyl-chromene by K. Shima, S. Hisada and I. Inagaki, *Yakugaku Zass.* 91 1124 (1971).

Addition to this chromene (60.40 g) dissolved in dimethyl sulphoxide (250 ml) containing water (10 ml) of N-bromosuccinimide (99.00 g) with vigorous stirring and cooling, followed by dilution with water and extraction via ethyl acetate, and recrystallisation from 60°–80° petroleum ether gave 6-carbomethyl-trans-3-bromo-3,4-dihydro-2,2-dihydro-2,2-dimethyl-2H-benzo-[b]pyran-4-ol (63.02 g) m.p. 88°–90° C. The bromohydrin (36.00 g) was vigorously stirred in dry ether (2.5 liters) containing potassium hydroxide pellets (36.00 g) for 3.75 days at room temperature. Filtration and evaporation followed by recrystallisation from 60°–80° petroleum ether yielded 6-carbomethoxy-trans-3,4-epoxy-3,4-dihydro-2,2-dimethyl-2H-benzo[b]pyran as white needles of m.p. 51°–52° C. (19.55 g).

This epoxide (19.55 g) and pyrrolidine (8.35 ml) were refluxed in ethanol (350 ml) for 22 hours. Removal of solvent gave a crude solid (25.34 g) part of which (15.27 g) was dissolved in ethanol (80 ml) and treated with methane sulphonic acid (3.40 ml). Addition of ether (200 ml) gave crystalline material which was recrystallised from ethanol-diethyl ether as white needles being 6-carbomethoxy-3,4-dihydro-2,2-dimethyl-trans-4-pyrrolidino-2H-benzo[b]pyran-3-ol methane sulphonate (16.30 g) of m.p. 138°–140° C.

EXAMPLE 5

6-Carbamoyl-3,4-dihydro-2,2-dimethyl-trans-4-piperidino-2H-benzo[b]pyran-3-ol and
6-Carbamoyl-3,4-dihydro-2,2-dimethyl-trans-4-isopropylamino-2H-benzo[b]pyran-3-ol methane sulphonates To trans-4-piperidino-3,4-dihydro-2,2-dimethyl-6-cyano-2H-benzo[b]pyran-3-ol hydrochloride (0.70 g) stirred in t-butanol (10 ml) was added finely powdered potassium hydroxide (1.5 g). The mixture was refluxed for 50 minutes and after cooling poured into brine (25 ml) and the solution extracted with chloroform (3 × 10 ml). The combined extracts were dried, and removal of drying agent and solvent gave a pale yellow solid (0.32 g) of m.p. 229°–230° C. Some of this solid (0.25 g) dissolved in ethanol and treated with methanesulphonic acid (0.06 ml) and ether. A gum formed which solidified after decanting off solvent and adding dry ether. Three recrystallisations from ethanol-ether gave 6-carbamoyl-3,4-dihydro-2,2-dimethyl-trans-4-piperidino-2H-benzo[b]pyran-3-ol methane sulphonate (0.22 g) a white solid of m.p. 229°–230° C.

Similarly prepared from trans-4-isopropylamino-3,4-dihydro-2,3-dimethyl-6-cyano-2H-benzo[b]pyran-3-ol hydrochloride (0.70 g) gave 6-carbamoyl-3,4-dihydro-2,2dimethyl-trans-4-isopropylamino-2H-benzo[b]pyran-3-ol methane sulphonate (0.27 g) as a white solid of m.p. 176°–177° C. from ethanol-ether.

EXAMPLE 6

Biological Data

The following results were obtained after oral administration in DOCA-salt treated hypertensive rats [method of I. M. Claxton, M. G. Palfreyman, R. H. Poyser and R. L. Whiting, *European Journal of Pharmacology*, 37, 179 (1976)] or spontaneously hypertensive rats (SHR) at the following doses:

| Compound of Example No. | Time Post Dose (hrs.) | % Change in Systolic Blood Pressure | % Change in Heart Rate |
| --- | --- | --- | --- |
| 1(1) at 100mg/kg (DOCA) | 1 | −58 | +58 |
|  | 2 | −47 | +34 |
|  | 4 | −37 | +17 |
|  | 6 | −49 | +25 |
|  | 24 | −24 | +13 |
|  | 48 | −14 | +1 |
| 2 at 100mg/kg (DOCA) | 1 | −33 | +27 |
|  | 2 | −31 | +24 |
|  | 4 | −37 | +31 |
|  | 6 | −31 | +27 |
|  | 24 | −7 | −4 |
| 4 at 10mg/kg (SHR) | 1 | −27 | +10 |
|  | 2 | −23 | +5 |
|  | 4 | −15 | −1 |
|  | 6 | −11 | −1 |
|  | 24 | +3 | −10 |
| 5 at 100mg/kg (SHR) | 1 | −21 | +2 |
|  | 2 | −40 | +2 |
|  | 4 | −20 | −3 |
|  | 6 | −20 | −3 |
|  | 24 | +1 | −9 |
| 3 at 100mg/kg (DOCA) | 1 | −13 | +3 |
|  | 2 | −32 | +3 |
|  | 4 | −24 | +3 |
|  | 6 | −18 | +4 |
|  | 24 | −5 | −9 |

The compounds tested did not have a high level of acute toxicity, for example oral $LD_{50}$ values greater than 200 mg/kg are to be expected.

EXAMPLE 7

The intermediate cyano compounds of Example 5 may be prepared as follows:

4-Cyanophenol (19.6 g), sodium hydroxide pellets (9.9 g), 3-chloro-3-methylbut-1-yne (40.83 g) and benzyltrimethyl-ammonium hydroxide (34.5 g, 40% in methanol) were stirred in methylene chloride (150 ml) and water (150 ml) at room temperature for 4 days. After separation of the layers, the aqueous layer was extracted twice with chloroform. The combined organic extracts were evaporated and the residue taken up in ether and washed with water and 2N sodium hydroxide solution before drying over anhydrous sodium sulphate. Removal of solvent and drying agent gave an oil (15.72 g). Distillation at 0.5 mm Hg gave the analytical material as the fraction boiling at 96°–102° C. (10.13 g).

Cyclisation of the 3-(p-cyanophenoxy)-3-methybut-1-yne (9.77 g) was accomplished by heating in diethylaniline at 210°–220° C. under nitrogen. Purification by distillation, and extraction with dilute hydrochloric acid gave 2,2-dimethyl-6-cyano-2H-benzo[b]pyran as a colourless oil (6.84 g), which slowly crystallised on standing, having a nmr spectrum showing signals at δ1.46, 6.25 (d, J=10), 5.67 (d, J=10), 6.74 (d, J=8), 7.18 (d, J=2), 7.34 (q, J=8,2)

To a stirred cooled solution of 2,2-dimethyl-6-cyano-2H-benzo[b]pyran (6.56 g) in dimethyl sulphoxide (65 ml) and water (1.30 ml) was added freshly crystallised N-bromosuccinimide (12.63 g) in one portion. Dilution with water after stirring for an additional 1 hour, and insolation via ethyl acetate gave trans-3-bromo-3,4-dihydro-2,2-dimethyl-6-cyano-2H-benzo[b]pyran-4-ol as a white crystalline solid (10.54 g), a small portion of which recrystallised from 60–80 petroleum ether had m.p. 128°–128.5° C.

This bromohydrin (5.63 g) was stirred with sodium hydroxide (0.80 g) in dioxan (75 ml) and water (18 ml) at room temperature for 3 hours. Work up by dilution and extraction with ethyl acetate gave 3,4-epoxy-3,4-dihydro-2,2-dimethyl-6-cyano-2H-benzo[b]-pyran (4.35 g) as a colourless oil having signals at δ1.26 and 1.54 (—CH$_3$), 3.80 (d, J=4,H-4), 3.40 (d, J=4, H-3), 6.77 (d, J=8, H-8), 7.43 (q, J=8,2,4.7) and 7.58 (d, J=2, H-5) in its nmr spectrum.

Treatment of 3,4-epoxy-3,4-dihydro-2,2-dimethyl-6-2H-benzo[b]pyran (2.09 g) with piperidine (0.86 g) in refluxing ethanol (60 ml) for 24 hours followed by evaporation of solvent gave a yellow oil which was dissolved in the minimum quantity of ethanol and treated with ethereal hydrogen chloride to give crystals of trans-4-piperidino-3,4-dihydro-2,2-dimethyl-6-cyano-2H-benzo[b]pyran-3-ol hydrochloride on standing (2.06 g) of m.p. 253°–257° C.

Similarly prepared for the epoxide was trans-4-isopropylamino-3,4-dihydro-2,2-dimethyl-6-cyano-2H-benzo[b]pyran-3-ol hydrochloride m.p. 251° C.

What we claim is:

1. A compound selected from the group consisting of (a) a 3,4-dihydro-2H-benzo[b]pyran of the formula:

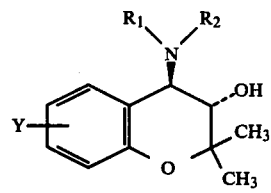

wherein $R_1$, when taken independently of $R_2$, is hydrogen or alkyl of up to 4 carbon atoms, unsubstituted or substituted with chloro, bromo, hydroxy, alkoxy of up to 4 carbon atoms or alkanoyloxy of up to 4 carbon atoms;

$R_2$, when taken independently of $R_1$, is hydrogen or alkyl of up to 4 carbon atoms;

$R_1$ and $R_2$ taken together, together with the nitrogen atom to which they are bound, are pyrrolidino, piperidino or hexamethyleneimino, unsubstituted or substituted with one or two methyl groups; and Y is $COR_3$, $COOR_3$, $SOR_3$, $SO_2R_3$, $SOOR_3$, $SO_2OR_3$, $CH(OH)R_3$, $C(R_3)=NOH$, $C(R_3)=NNH_2$, $CONH_2$, $CONR_4R_5$, $SONR_4R_5$ or $SO_2NR_4R_5$ in which:

each of $R_3$ and $R_4$ is independently alkyl of up to 8 carbon atoms, unsubstituted or substituted with chloro, bromo, hydroxy, alkoxy of up to 4 carbon atoms or alkanoyloxy of up to 4 carbon atoms or substituted with three fluoro on the same carbon atom and $R_5$ is hydrogen or alkyl of up to 4 carbon atoms, (b) an O-alkanoyl derivative thereof, said alkanoyl having up to 6 carbon atoms and being unsubstituted or substituted with phenyl, and (c) a pharmaceutically acceptable acid addition salts thereof.

2. A compound according to claim 1 wherein Y is $COR_3$, $COOR_3$, $SOR_3$, $SO_2R_3$, $SOOR_3$, $SO_2OR_3$, $CONR_4R_5$, $SONR_4R_5$ or $SO_2NR_4R_5$, wherein each of $R_3$ and $R_4$ is methyl or ethyl.

3. A compound according to claim 2 wherein Y is $COR_3$, $COOR_3$ or $CONR_4R_5$.

4. A compound according to claim 2 wherein Y is $SO_2R_3$, $SO_2OR_3$ or $SO_2NR_4R_5$.

5. A compound according to claim 1 wherein Y is $CH(OH)R_3$, $C(R_3)=NOH$ or $C(R_3)=NNH_2$.

6. A compound according to claim 1 wherein $R_1$ is hydrogen and $R_2$ is methyl, ethyl, isopropyl or t-butyl.

7. A compound according to claim 1 wherein $R_1$ and $R_2$ together with the nitrogen atom to which they are bound are pyrrolidino or piperidino.

8. A compound according to claim 7 wherein Y is $COR_3$, $COOR_3$ or $CONR_4R_5$.

9. A compound according to claim 8 wherein Y is in the 6-position.

10. A compound according to claim 9, wherein Y is a $CO_2R_3$ group.

11. A compound according to claim 10 wherein $R_3$ is methyl.

12. A compound according to claim 7 wherein Y is $SO_2R_3$, $SO_2OR_3$ or $SO_2NR_3R_4$.

13. A compound according to claim 1 wherein Y is in the 6- or 7-position.

14. A compound according to claim 1 wherein Y is in the 6-position.

15. A compound according to claim 1 which is the O-alkanoyl derivative as therein defined.

16. A compound according to claim 15 which is an O-acetyl derivative.

17. A compound according to claim 1 which is in the form of a pharmaceutically acceptable acid addition salt.

18. The compound according to claim 1 which is 6-acetyl-3,4-dihydro-2,2-dimethyl-trans-4-piperidino-2H-benzo [b]pyran-3-ol or a pharmaceutically acceptable acid addition salt thereof.

19. The compound according to claim 1 which is 6-acetyl-3,4-dihydro-2,2-dimethyl-trans-4-pyrrolidino-2H-benzo [b]pyran-3-ol or a pharmaceutically acceptable acid addition salt thereof.

20. The compound according to claim 1 which is 6-acetyl-3,4-dihydro-2,2-dimethyl-trans-4-isopropylamino-2H-benzo [b]pyran-3-ol or a pharmaceutically acceptable acid addition salt thereof.

21. The compound according to claim 1 which is 6-carbomethoxy-3,4-dihydro-2,2-dimethyl-trans-4-piperidino-2H-benzo[b]pyran-3-ol or a pharmaceutically acceptable acid addition salt thereof.

22. The compound according to claim 1 which is 6-carbomethoxy-3,4-dihydro-2,2-dimethyl-trans-4-pyrrolidino-2H-benzo[b]pyran-3-ol or a pharmaceutically acceptable acid addition salt thereof.

23. The compound according to claim 1 which is 6-carbomethoxy-3,4-dihydro-2,2-dimethyl-trans-4-isopropylamino-2H-benzo[b]pyran-3-ol or a pharmaceutically acid salt thereof.

24. The compound according to claim 1 which is 1-(2,2-dimethyl-trans-3-hydroxy-4-piperidinochroman-6-yl)ethanone oxime or a pharmaceutically acceptable acid addition salt thereof.

25. The compound according to claim 1 which is 1-(2,2-dimethyl-trans-3-hydroxy-4-isopropylaminochroman-6-yl) ethanone oxime or a pharmaceutically acceptable acid addition salt thereof.

26. The compound according to claim 1 which is 1-hydroxy-1-(2,2-dimethyl-trans-3-hydroxy-4-piperidinochroman-6-yl)ethane or a pharmaceutically acceptable acid addition salt thereof.

27. The compound according to claim 1 which is 1-hydroxy-1-(2,2-dimethyl-trans-3-hydroxy-4-pyrrolidinochroman-6-yl)ethane or a pharmaceutically acceptable acid addition salt thereof.

28. The compound according to claim 1 which is 6-carbamoyl-3,4-dihydro-2,2-dimethyl-trans-4-piperidino-2-H-benzo[b]pyran-3-ol or a pharmaceutically acceptable acid addition salt thereof.

29. The compound according to claim 1 which is 6-carbamoyl-3,4-dihydro-2,2-dimethyl-trans-4-isopropylamino-2H-benzo[b]-pyran-3-ol or a pharmaceutically acceptable acid addition salt thereof.

30. A hypotensive pharmaceutical composition comprising a hypotensive amount of a compound according to claim 1 in combination with a pharmaceutically acceptable carrier.

31. The method of treating hypotension in a human or animal which comprises administering thereto a hypotensively effective amount of a compound according to claim 1.

* * * * *